United States Patent [19]

Anello et al.

[11] 4,377,716

[45] Mar. 22, 1983

[54] METHOD FOR THE PRODUCTION OF HEXAFLUORO-2,3-BIS(TRIFLUOROMETHYL)-2-BUTENE

[75] Inventors: Louis G. Anello, Hamburg; Richard F. Sweeney, Elma, both of N.Y.

[73] Assignee: Allied Corporation, Morris Township, Morris County, N.J.

[21] Appl. No.: 330,067

[22] Filed: Dec. 14, 1981

[51] Int. Cl.$^3$ ............................................. C07C 17/00
[52] U.S. Cl. .................................................. 570/153
[58] Field of Search ......................................... 570/153

[56] References Cited

U.S. PATENT DOCUMENTS 3,655,786  4/1972  Gilbert et al. ...................... 570/153

*Primary Examiner*—Charles F. Warren
*Assistant Examiner*—Joseph A. Boska
*Attorney, Agent, or Firm*—Jay P. Friedenson

[57] ABSTRACT

Hexafluoro-2,3-bis(trifluoromethyl)-2-butene may be prepared by heating 2,2,4,4-tetrakis-(trifluoromethyl)-1,3-dithietane at elevated temperatures in the presence of activated carbon. The activated carbon serves as a desulphurization catalyst.

7 Claims, No Drawings

METHOD FOR THE PRODUCTION OF HEXAFLUORO-2,3-BIS(TRIFLUOROMETHYL)-2-BUTENE

DESCRIPTION

TECHNICAL FIELD

This invention relates to a method for the production of hexafluoro-2-3-bis(trifluoromethyl)-2-butene which comprises heating 2,2,4,4-tetrakis-(trifluoromethyl)-1,3-dithietane at elevated temperatures in the presence of activated carbon.

BACKGROUND OF THE INVENTION

Hexafluoro-2,3-bis(trifluoromethyl)-2-butene (HFBTB) is a known compound which is useful as an environmentally acceptable solvent as a replacement for those applications in which 1,1,2-trichloro-1,2,2-trifluoroethane has been used. HFBTB is also useful as a refrigerant and is further useful as an intermediate to hexafluoroacetone by oxidation.

HFBTB has been prepared by the liquid phase fluorination of 2-chloroperfluoropropene with elemental fluorine followed by dechlorination of the resulting dimer addition product with zinc (W. T. Miller et al., *Ind. & Eng. Chem. Vol.* 39, 401 1947). This preparation suffers from the disadvantage of the need for expensive fluorine and the attendant disadvantage of a low temperature, liquid phase batch operation with low conversions and yields.

It is accordingly an object of the invention to provide a novel gas phase method for making HFBTB by a gas phase reaction susceptible of continuous operation which does not suffer from the above-noted disadvantages of the prior art method.

Other objects and advantages of the invention will become apparent from the following description.

SUMMARY OF THE INVENTION

In accordance with the invention, it has been surprisingly found that activated carbon promotes the desulphurization of 2,2,4,4-tetrakis-(trifluoromethyl)-1,3-dithietane (TTDT) by an easily controllable gas phase catalytic procedure in which (HFBTB) is prepared in good yields. Accordingly, in accordance with the invention, HFBTB is produced by heating TTDT at elevated temperatures in the presence of activated carbon.

DETAILED DESCRIPTION OF THE INVENTION AND OF THE PREFERRED EMBODIMENTS

The process of the invention may be conducted in continuous fashion by continuously passing the starting material TTDT vapor at elevated temperatures over activated carbon. Preferably, a tubular reactor is employed which may be constructed of Alundum, nickel, Monel, Inconel or stainless steel. Exit gases may be suitably cooled to trap all products and the products are fractionally distilled. The products recovered by distillation are $(CF_3)_2C=CF_2$ (b.p. 8° C.), $CF_3SSCF_3$ (b.p. 34° C.), the desired HFBTB product $(CF_3)_2C=C(CF_3)_2$ (b.p. 54.5° C.) and unreacted TTDT starting material (b.p. 110° C.).

Any of the well known activated carbon materials may be used in practice of the invention. Activated carbon is an amorphous form of carbon characterized by high adsorptivity for many gases, vapors and colloidal solids. The carbon is obtained by the destructive distillation of wood, nut shells, animal bones or other carbonaceous material. It is "activated" by heating to 800°–900° C. with steam or carbon dioxide which results in a porous internal structure. (*The Condensed Chemical Dictionary*, 9th Ed., p. 163).

A variety of activated carbons are commercially available under trademarks and grades such as Columbia MBV, Columbia MBQ, Columbia JXC, Columbia SBV, Barneby Cheney NB and Darco. The source or grade of the activated charcoal is not critical to the invention, however, the preferred form is granules to facilitate use in tubular reactors.

The size of the granules of the activated carbon employed is not critical. Since the reaction is preferably carried out in elongated tubular reactors; it is desirable to employ activated carbon granules of an average mesh size (U.S. Standard) between about 1/25 and ¼ of the reactor diameter. Most preferred conditions are those in which the reactor is substantially completely filled with activated carbon of an average mesh size of between about 1/6–1/10 of the reactor diameter.

The reaction zone temperatures should be elevated but operable temperatures lie over a wide range. The preferred temperature range is between about 250°–500° C. Still preferred are reaction temperatures in the range of about 350°–450° C. and most preferred are temperatures in the range of about 375°–425° C.

Contact or retention time of the TTDT with the activated carbon catalyst is not critical since appreciable conversions of product are obtained even at very short contact times, for example, in the order of about 0.5 second. Best results, however, are obtained in the range of about 1–60 seconds although much longer contact times can be employed such as five minutes or more without deleterious effects.

The method of the invention is most conveniently carried out at atmospheric pressure. Higher or lower pressures may be employed, however, without any particular advantage.

The following examples are illustrative of the practice of the invention. Parts and percentages are by weight and mesh sizes are U.S. Standard.

EXAMPLE I 145 ml of Columbia JXC activated carbon granules (4–6 mesh) were charged to a one inch I.D. Monel tubular reactor, 27" long, heated externally over about 24" inches of its length by an electric furnace provided with an automatic temperature control. Columbia JXC activated carbon is available from Union Carbide Corporation. It is a form of activated carbon derived from petroleum residue. The activated carbon granules have an average mesh size of about 1/6.6 of the reactor diameter. Over a period of 4 hours, 478 grams (1.31 moles) of TTDT $[(CF_3)_2C-S]_2$, were passed over the catalyst at a reaction temperature of 425° C. for a retention time of about 25 seconds. Exit products from the reactor were passed into a dry ice acetone cold trap. Fractional distillation of the 441 grams of the cold trap product effected recovery of 24.3 grams (0.12 mole, 15.4% yield) of $(CF_3)_2C=CF_2$, 14.5 grams (0.071 mole, 9% yield) of $CF_3SSCF_3$, 86 grams (0.31 mole, 39.1% yield) of the desired $(CF_3)_2C=C(CF_3)_2$ product and 191.3 grams (0.52 mole) of unreacted $[(CF_3)_2C-S]_2$. Thus, of the starting material fed, 23.6% was converted to the desired $(CF_3)_2C=C(CF_3)_2$. The NMR and IR of the $(CF_3)_2C=C(CF_3)_2$ recovered were consistent with the expected structure.

EXAMPLE II

Following the procedure of Example I and with the same apparatus, 411 grams (1.11 moles) of $[(CF_3)_2C\text{-}S]_2$ were passed over the activated carbon catalyst over a period of four hours at a reaction temperature of 450° C. and a retention time of 26 seconds. Fractional distillation of the 372.4 grams of cold trap product effected recovery of 33.5 grams (0.17 mole, 19.2% yield) of $(CF_3)_2C=CF_2$, 26 grams (0.13 mole, 15% yield) of $CF_3SSCF_3$, 66 grams (0.22 mole, 25.2% yield) of the desired $(CF_3)_2C=C(CF_3)_2$ product and 87 grams (0.24 mole) of unreacted $[(CF_3)_2C\text{-}S]_2$. The conversion to $(CF_3)_2C=C(CF_3)_2$ was 20% based on the starting material fed. The NMR and IR of the $(CF_3)_2C=C(CF_3)_2$ recovered were consistent with the expected structure.

EXAMPLE III

Following the procedure of Example I and with the same apparatus, 343 grams (0.94 mole) of $[(CF_3)_2C\text{-}S]_2$ were passed over 145 ml of Columbia MBV carbon over a period of 3.75 hours, at a reaction temperature of 425° C. and a retention time of about 25 seconds. Columbia MBV activated carbon is available from Union Carbide Corporation. It is a form of activated carbon derived from bituminous coal. The activated carbon granules have an average mesh size of about 1/6.6 of the reactor diameter. Fractional distillation of the 324.5 grams of the cold trap product effected recovery of 9.7 grams (0.05 mole, 7.6% yield) of $(CF_3)_2C=CF_2$, 12.3 grams (0.06 mole, 9.6% yield) of $CF_3SSCF_3$, 71.5 grams (0.24 mole, 38% yield) of the desired $(CF_3)_2C=C(CF_3)_2$ product and 111 grams (0.31 mole of unreacted $[(CF_3)_2C\text{-}S]_2$. The conversion to $(CF_3)_2C=C(CF_3)_2$ based on the starting material fed was 25.2%. The NMR and IR of the $(CF_3)_2C=C(CF_3)_2$ recovered were consistent with the expected structure.

EXAMPLE IV

Following the procedure of Example I and with the same apparatus, 346 grams (0.95 mole) of $[(CF_3)_2C\text{-}S]_2$ were passed over 145 ml of Columbia SBV activated carbon granules (4-6 mesh) over a period of 3 hours at a reaction temperature of 425° C. and a retention time of 25 seconds. Columbia SBV activated carbon is available from Union Carbide Corporation. It is a form of activated carbon derived from coconut shells. The activated carbon granules have an average mesh size of about 1/6.6 of the reactor diameter. Fractional distillation of the cold trap products effected recovery of 16.3 grams (0.08 mole, 11% yield) of $(CF_3)_2C=CF_2$, 12 grams (0.06 mole, 8% yield) of $CF_3SSCF_3$, 84.2 grams (0.28 mole, 38.3% yield) of the desired $(CF_3)_2C=C(CF_3)_2$ and 80.0 grams (0.22 mole) of unreacted $[(CF_3)_2C\text{-}S]_2$. The conversion to $(CF_3)_2C=C(CF_3)_2$ based on the starting material fed was 29.4%. The NMR and IR of the $(CF_3)_2C=C(CF_3)_2$ recovered were consistent with the expected structure.

EXAMPLES V-X

The procedure of Example I is repeated in the same apparatus excepting that catalyst and conditions are varied as shown in the following table. In all cases $(CF_3)_2C=C(CF_3)_2$ product is obtained in good yields and conversions.

| Example | Catalyst | Catalyst/Reactor Diameter Ratio | Temperature (°C.) |
|---|---|---|---|
| V | Columbia MBQ* | 1/6 | 250 |
| VI | Darco | 1/10 | 500 |
| VII | Barneby Cheney NB** | 1/25 | 350 |
| VIII | Columbia MBV | 1/4 | 450 |
| IX | Columbia MBQ | 1/6 | 375 |
| X | Columbia SBV | 1/10 | 425 |

*Derived from bituminous coal.
**Derived from hardwood charcoal.

We claim:

1. A method for the production of hexafluoro-2,3-bis(trifluoromethyl-2-butene which comprises heating 2,2,4,4-tetrakis(trifluoromethyl)-1,3-dithietane in the presence of activated carbon.

2. A method according to claim 1 in which the activated carbon comprises granules and in which the elevated temperatures are between about 250°-500° C.

3. A method according to claim 2 in which the elevated temperatures are between about 350°-450° C.

4. A method according to claim 2 in which the elevated temperatures are between about 375°-425° C.

5. A method according to claim 2 in which the activated carbon comprises granules of an average mesh size between about 1/25 and ¼ of the diameter of the reactor employed.

6. A method according to claim 2 in which the activated carbon comprises granules of an average mesh size between about 1/6 and 1/10 of the diameter of the reactor employed.

7. A method according to claim 6 in which the elevated temperatures are between about 375°-425° C.

* * * * *